(12) United States Patent
Hahn et al.

(10) Patent No.: US 8,495,901 B2
(45) Date of Patent: Jul. 30, 2013

(54) SHAPING TOOL HAVING A ROTATABLE BASE MEMBER

(75) Inventors: Christoph Hahn, Sprendlingen (DE);
Gerald Mathe, Waldalgesheim (DE);
Michael Huebner,
Bacharach-Henschhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 360 days.

(21) Appl. No.: 12/748,772

(22) Filed: Mar. 29, 2010

(65) Prior Publication Data

US 2010/0242954 A1    Sep. 30, 2010

(30) Foreign Application Priority Data

Mar. 30, 2009    (EP) .................................... 09156671

(51) Int. Cl.
*B21D 1/02*    (2006.01)
(52) U.S. Cl.
USPC ................. 72/214; 72/112; 72/122; 72/452.9
(58) Field of Classification Search
USPC .......... 72/67, 112, 115, 122–124, 214, 452.8, 72/452.9
See application file for complete search history.

(56) References Cited

U.S. PATENT DOCUMENTS

| 3,953,995 A | 5/1976 | Haswell et al. | |
| 5,697,242 A * | 12/1997 | Halasz et al. | 72/117 |
| 2003/0194379 A1 | 10/2003 | Brugger et al. | |
| 2004/0194524 A1 * | 10/2004 | Jentzsch | 72/123 |
| 2010/0242557 A1 * | 9/2010 | Spreitzer et al. | 72/123 |

FOREIGN PATENT DOCUMENTS

| EP | 0642992 A2 | 3/1995 |
| EP | 0916428 A2 | 5/1999 |
| EP | 1025923 A1 | 8/2000 |
| FR | 2505688 A1 | 11/1982 |
| GB | 2101020 A | 1/1983 |
| GB | 2355252 A | 4/2001 |
| JP | 2005144459 A | 6/2005 |
| WO | 8200785 A1 | 3/1982 |
| WO | 03059547 A1 | 7/2003 |
| WO | 2008146025 A2 | 12/2008 |
| WO | 2009006137 A1 | 1/2009 |

OTHER PUBLICATIONS

JP2005144459—English language abstract only.

* cited by examiner

*Primary Examiner* — Dana Ross
*Assistant Examiner* — Pradeep C Battula
(74) *Attorney, Agent, or Firm* — Michael P. Morris; Anthony P. Bottino

(57) ABSTRACT

A shaping tool as depicted in exemplary FIG. 3 comprising a rotatable base member having at least one profiled bending roller (13) which is mounted on a circular track and is rotatable about a rotation axis. The bending roller (13) arranged on a radially movable slide (11) is movable from a position defining a maximum working aperture for the tool, by means of a spring-loaded lever (9) which has an axial configuration, into a position defining a minimum working aperture for the tool.

11 Claims, 3 Drawing Sheets

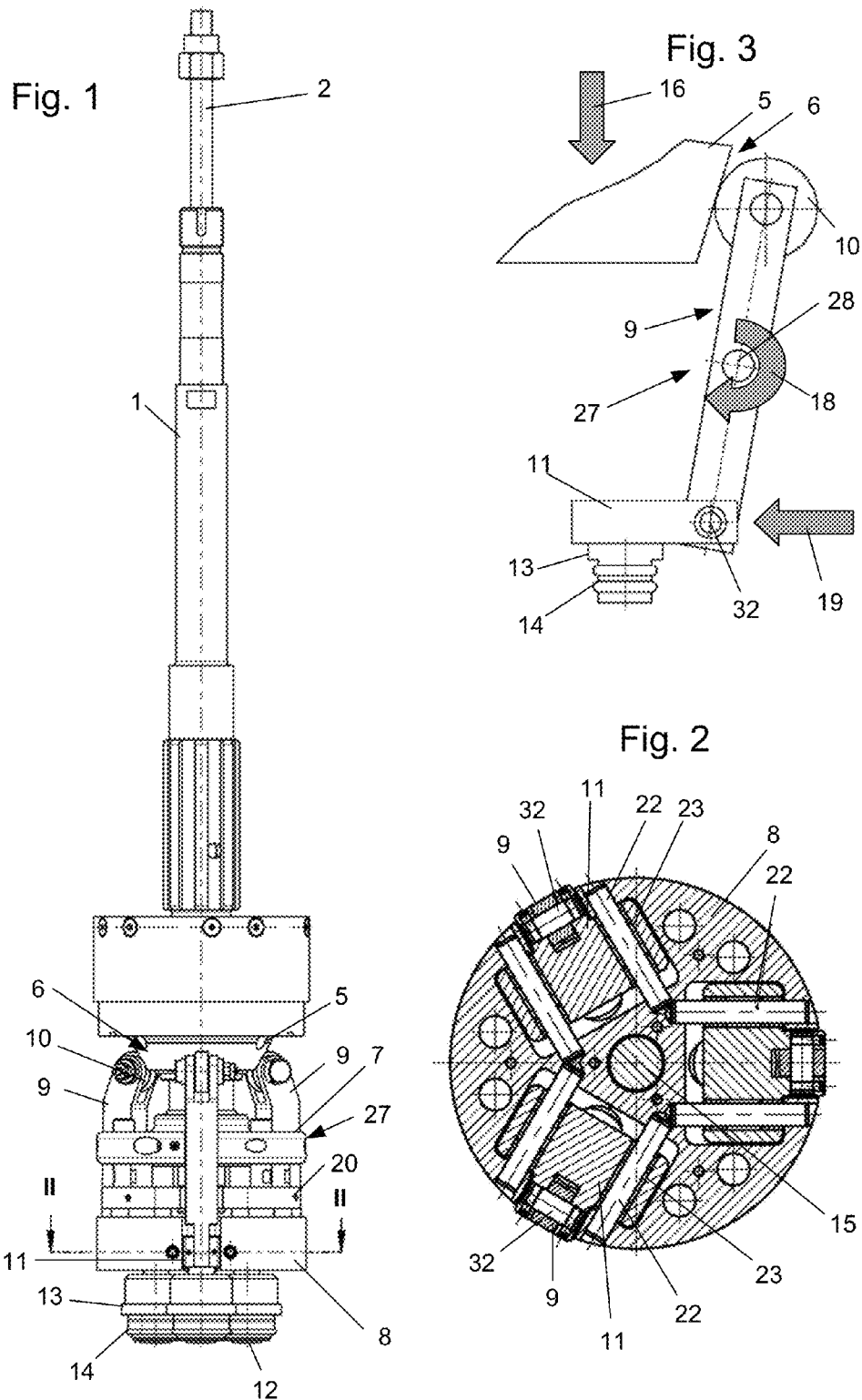

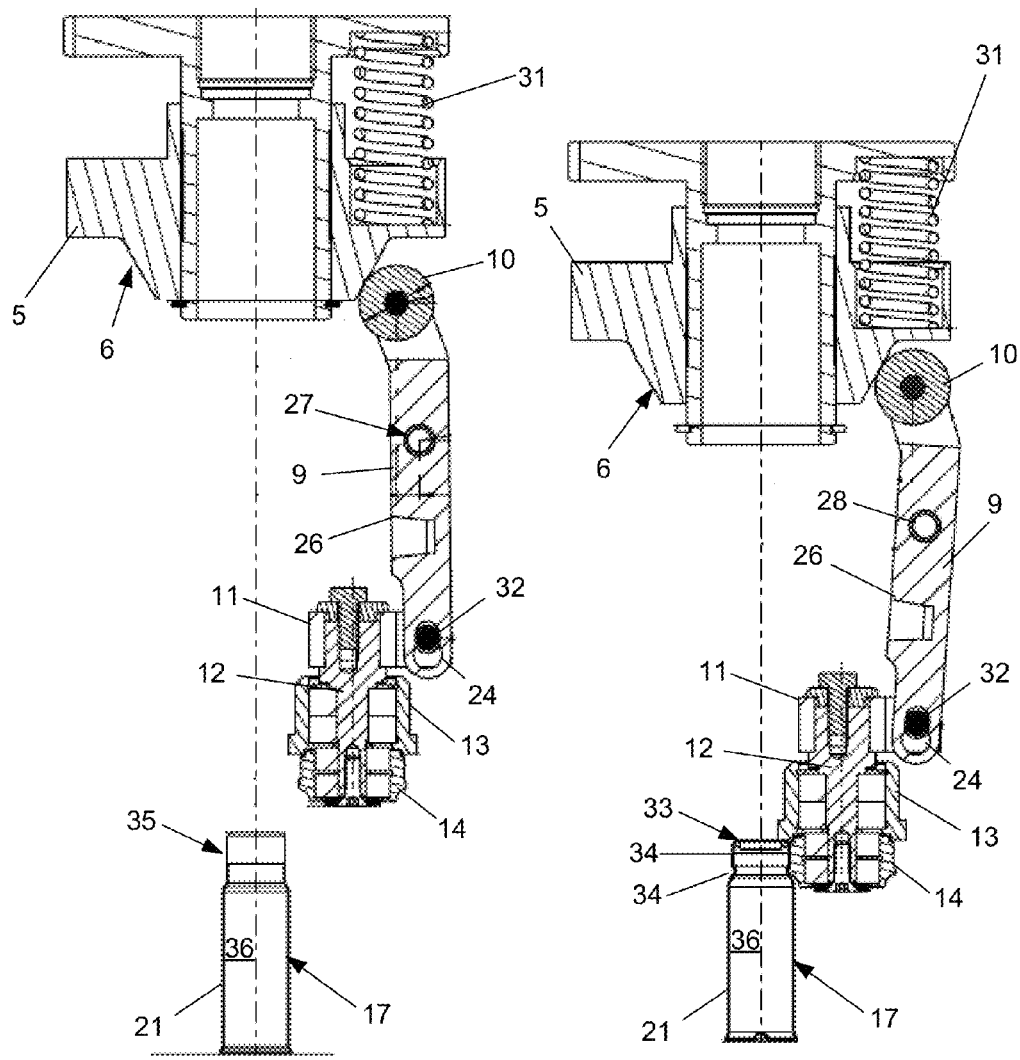
Fig. 4                    Fig. 5

SHAPING TOOL HAVING A ROTATABLE BASE MEMBER

The invention relates to a shaping tool which comprises a rotatable base member having at least one profiled bending roller which is mounted on a circular track and is rotatable about a rotation axis.

BACKGROUND OF THE INVENTION

For administering inhalable pharmaceutical formulations of active substances, the patient uses hand-held, manually operated inhalers in which the pharmaceutical active substance formulation is contained in an inhaler cartridge. The inhaler cartridge consists of an external aluminium cartridge and a plastic container inserted therein, the plastic container being produced by co-extrusion and comprising a rigid outer container and a flexible inner pouch disposed inside it. In order to create a pressure equalisation opening between the inner pouch and the outer container, an opening is formed in the relatively rigid outer container by the so-called cut-crack-open process, for example. The plastic container is filled with the pharmaceutical active substance formulation and sealed, and inserted into the aluminium cartridge during the manufacturing process to form the inhaler cartridge. In a subsequent step, a deformed wall region is formed in the aluminium cartridge in the upper region of the inhaler cartridge thus assembled, this deformed region bearing on the outer surface of the plastic container inserted in the aluminium cartridge. To form the attachment region on the upper edge of the aluminium cartridge a drawing process is used in which a rotating drawing tool moves with its working aperture for the tool from above over the attachment region to be formed on the aluminium cartridge and thereby brings profiled drawing rollers arranged around the working aperture for the tool into contact with the outer surface of the aluminium cartridge, in order to shape the attachment region by axial movement. Then in another manufacturing step the aluminium cartridge is applied in gastight manner against the outside of the plastic container disposed therein, which is filled with a pharmaceutical active substance formulation.

In the case of a shaping tool known in the art, comprising a rotatable base member with profiled bending rollers arranged on a circular track and rotatable about a rotation axis, the bending rollers are moved in a radial pivoting movement in one plane from a maximum working aperture for the tool into a minimum working aperture for the tool. This shaping tool has proved problematic in its reliability and susceptibility to breakdown.

SUMMARY OF THE INVENTION

The problem that the invention sets out to solve is to provide a shaping tool of the kind mentioned hereinbefore which is reliable in operation.

According to the invention the problem is solved by the fact that the bending roller arranged on a radially movable slide is movable from a position that defines a maximum working aperture for the tool, by means of a spring-loaded lever with an axial configuration, into a position that defines a minimum working aperture for the tool.

Since the shaping tool rotates, the workpiece, i.e. the inhaler cartridge which is to be produced, filled with a liquid active substance formulation, can be fixed in place, thereby preventing foaming of the active substance formulation. The shaping tool is positioned relative to the workpiece, while the bending roller is located in the position defining the maximum working aperture for the tool. By an adjusting movement using the lever, the bending roller is moved into the position defining the minimum working aperture for the tool. The profiled bending roller is matched to the contour that is to be produced and as a result of the radial adjustment an encircling radius, for example, is produced in rotationally symmetrical manner on an upper edge of the obviously cylindrical workpiece, whereby after an initial adjustment or determination of the diameter of the minimum working aperture for the tool a reliable product which is accurate in its shape and dimensions is obtained. The resetting of the bending roller from the minimum working aperture for the tool to the maximum working aperture for the tool is carried out by means of a radially acting compression spring.

According to a further feature, in the center, an axially acting depressor for the clamped workpiece is provided and a pressing member that is conical at least in parts is axially movable under spring loading relative to the depressor, while the pressing member cooperates with one end of the lever in order to move the bending roller into the minimum working aperture for the tool. When the rotating shaping tool moves axially downwards, first of all the depressor makes contact with the workpiece, which consists of an aluminium cartridge with a plastic container inserted therein. The depressor presses the plastic container into the aluminium cartridge and holds the workpiece. Thus the depressor performs the function of positioning the plastic container in the aluminium cartridge. At this height in which the depressor secures the workpiece in the axial direction, the bending roller is also positioned at the required height. During further downward motion the pressing member is moved downwards and the cone of the pressing member acts upon the lever in order to shift the bending roller in the radial direction into the position of the minimum working aperture for the tool where the workpiece has its end contour. In the event of incorrect axial positioning, the pressing member would act upon the lever too early or too late, resulting in a defective and in particular non-gastight end contour.

In order to convert the axial movement of the pressing member into the radial direction of movement of the bending roller the lever is preferably provided, at its end facing the pressing member, with a roller that rolls on the pressing member and at its opposite end it is pivotably connected to the slide.

So that the bending roller comes to engage with the workpiece in a rectilinear motion, a cylindrical bolt is expediently inserted in a bore in the slide, on the one hand, and in an oblong hole in the lever, on the other. The minimum working aperture for the tool, which is determined by the radial position of the bending roller in the case of a pressing member that is moved relatively in the direction of the slide, can be fixed for example by varying the diameter of the roller associated with the lever which rolls on the pressing member and it is not absolutely necessary for the lever to be adjustable relative to the slide. The shaping of the bearing point by means of the inexpensive cylindrical bolt, which is fixed in the slide on the one hand and inserted in the oblong hole of the lever on the other hand, meets the requirements.

In order to achieve a defined deflection of the respective direction of movement reliably and reproducibly, the lever is preferably pivotably mounted on a carrier member. The carrier member is fixedly positioned relative to the slide in the axial direction and movable relative to the pressing member.

Preferably the pressing member is resiliently mounted in the axial direction. When the bending roller is in its radial end position, in which it describes the minimum working aperture for the tool and the final dimensions of the workpiece have been achieved, the pressing member moves counter to the spring force acting upon it, in order to prevent further advancing of the bending roller with resultant destruction of the workpiece. However with the spring-loaded overload prevention device it is also possible to generate the pressure needed to ensure the deformation and any tolerances in the workpiece can be equalised. The resilience associated with the pressing member may be effective both with an undersized workpiece and with an oversized one and will always clamp the bending roller against the workpiece. To provide the spring force, a central compression spring may be arranged or a plurality of compression springs uniformly distributed over the circumference of the pressing member may be provided.

According to one feature, at least one shaping roller for producing a crimp is rotatably mounted on an axis of the slide adjacent to the bending roller. Expediently, the slide is slidably mounted on two guide bolts spaced from each other in a guide portion, the guide portion being connected to the carrier member. Obviously, the slide may consist of a slidable material or have sliding bushes which run on the guide bolts, thereby largely ruling out any jamming.

For reproducibly adjusting the height of the shaping tool by simple means, a cam roller advantageously cooperates with a cam control for the axial movement of the shaping tool. The travel speeds and distances may be decided by means of the control cam of the cam control in known manner. The cam roller may be mounted in particular on a housing of the shaping tool.

Expediently, three radially adjustable slides each having one lever are arranged in a star shape with one another. The workpiece can be shaped relatively uniformly with the equidistantly distributed bending and shaping rollers and a high surface quality can be achieved at a high shaping speed while adhering to relatively narrow tolerances of form and dimensions.

A retaining device fixes the workpiece, which consists of an aluminium cartridge and a plastic container, coaxially with respect to a longitudinal axis along which the shaping tool travels vertically. The retaining device may be part of a conveying and/or packaging apparatus, for example in the form of a rotary plate machine or a conveyor belt.

The shaping tool described above is used for profiling a neck region of an inhaler cartridge which consists of an exterior aluminium cartridge and a plastic container placed therein which holds an active substance formulation. The plastic container can be produced by the co-extrusion method and may comprise a rigid outer container and a flexible inner pouch disposed therein. In the course of manufacture, the plastic container is filled with the pharmaceutical active substance formulation and sealed.

The inhaler cartridge manufactured with the shaping tool is used as a storage container in a nebuliser for dispensing a specified amount of a fluid, particularly one that contains a medicament, as an aerosol through a nozzle from a pressurised store, wherein a mechanical pressure generator acts upon the measured out fluid in the pressurised store which is to be released in one go for nebulisation. A known nebuliser is marketed by Boehringer Ingelheim KG under the brand name "Respimat" in the form of an inhaler and is shown in WO 91/14468 A1 and in WO 97/12687 A1.

It will be understood that the features mentioned above and to be explained hereinafter may be used not only in the particular combination specified but also in other combinations. The scope of the invention is defined only by the claims.

BRIEF DESCRIPTION OF THE DRAWINGS

The invention is hereinafter explained in more detail by means of two embodiments by way of example, by reference to the attached drawings, wherein:

FIG. 1 is a front view of a shaping tool according to the invention.

FIG. 2 is a sectional view of the shaping tool according to FIG. 1 on the line II-II.

FIG. 3 is a schematic partial representation of the shaping tool according to FIG. 1.

FIG. 4 is a partial representation of the shaping tool according to FIG. 1 in section.

FIG. 5 is another representation of the shaping tool according to FIG. 4 in section.

DETAILED DESCRIPTION OF THE INVENTION

Figure 6:
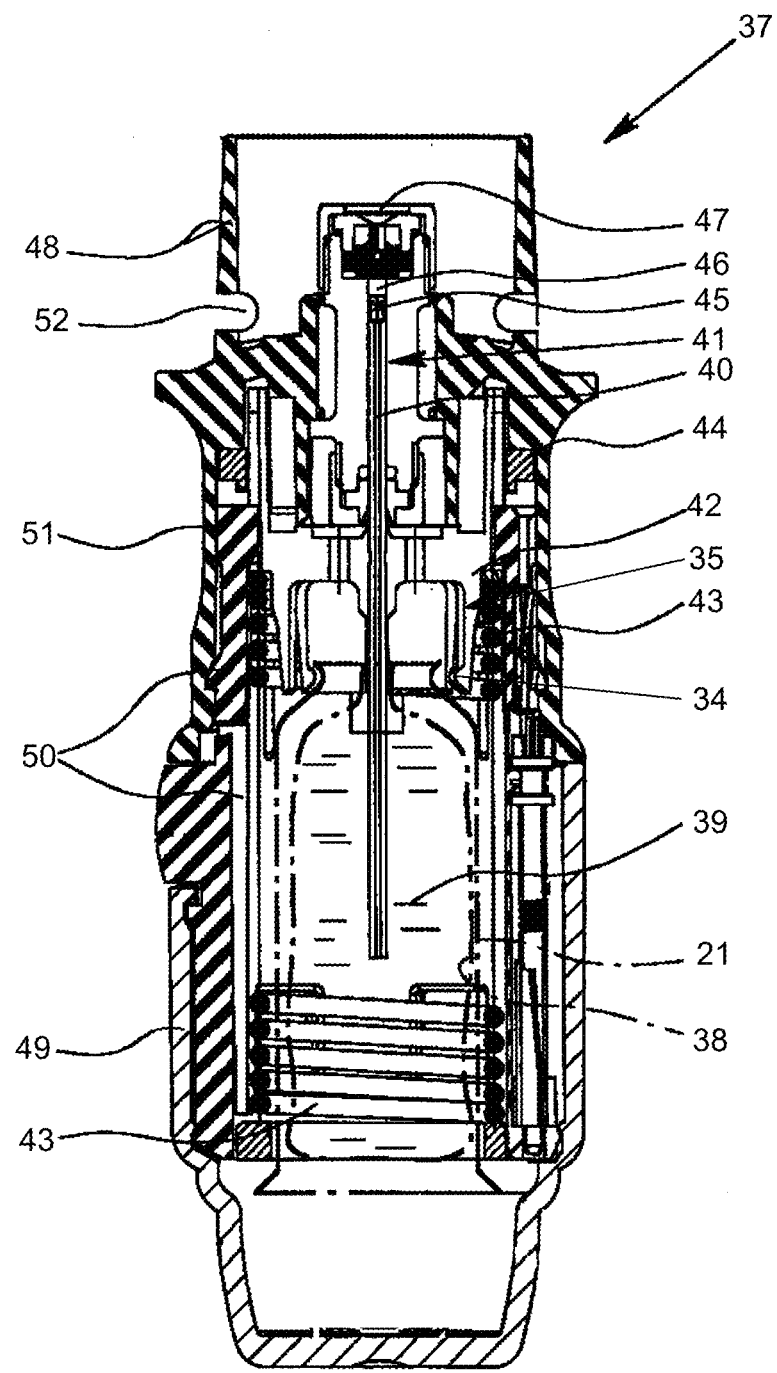
FIG. 6 is a representation of a nebuliser with an inhaler cartridge produced using the shaping tool according to FIG. 1, in section.

The shaping tool comprises a rod 2 mounted in a hollow shaft 1 and connected to a rotary drive (not shown). An axial up and down movement of the shaping tool is controlled by means of a radially mounted cam roller on the tool side, which cooperates with a cam control. In a housing (not shown) are various mounting, coupling and spring elements.

Underneath the housing is secured a pressing member 5 with a conical region 6 and underneath the pressing member 5 are a carrier member 7 and a guide portion 8, while pivotably mounted in the carrier member 7 are three levers 9 which comprise, at one end, rollers 10 cooperating with the pressing member 5, while the opposite ends from the rollers 10 act upon slides 11 mounted in the guide portion 8. Each of the slides 11 has a bending roller 13 and a shaping roller 14 on a spindle 12. For guiding the slide lithe guide portion 8 is fitted with guide bolts 22 aligned parallel and at a spacing from one another and the slides 11 are provided with sliding bushes 23 which run on the guide bolts 22. Obviously, the guide bolts 22 are aligned such that the slides 11 move in the radial direction.

By means of the pivotable levers 9, the bending rollers 13 can be moved out of a position that defines a maximum working aperture for the tool into a position that defines a minimum working aperture for the tool. Specifically, in a downward movement of the rotating shaping tool as indicated by the arrow 16, a depressor 15 first of all presses directly on a workpiece 17, namely an inhaler cartridge 36. As the downward movement continues, the levers 9 are pivoted in the direction of the arrow 18 as a result of the activity of the conical region 6 of the pressing member 5 and the pivoting movement of the lever 9 is converted into a radial advancing movement of the slide 11 in the direction of the arrow 19, in order to move the bending roller 13 and the shaping roller 14 into their end position in which they describe the minimum working aperture for the tool. When the shaping tool is moved axially upwards, the levers 9 are pivoted by means of radially acting compression springs supported on an intermediate ring 20 on the one hand and in a blind bore 26 of the associated lever 9 on the other hand, so that the bending roller 13 and the shaping roller 14 are moved into a position in which they describe the maximum working aperture for the tool.

In order to avoid damage to the workpiece 17, which consists of an aluminium cartridge 21 with a plastic container 38 inserted therein, and provide equalisation of tolerances for different workpiece dimensions, the pressing member 5 is mounted to be axially movable, through being spring-loaded by compression springs 31, a plurality of compression springs 31 being uniformly distributed. During axial movement of the pressing member 5 in the direction of the workpiece 17, the roller 10 of the lever 9 travels over the conical region 6 of the pressing member 5 and the one-piece lever 9 swivels counter to the action of the radially acting restoring spring about the swivel joint 27, which comprises a pin 28 engaging in the carrier member 7. At the same time a cylindrical bolt 32 inserted in the slide 11 slides in an oblong hole 24 in the lever 9, as a result of which the slide 11 is moved radially towards the workpiece 17. Once the bending roller 13 and the shaping roller 14 have reached their end positions, the pressing member 5 is moved counter to the action of the compression springs 31 relative to the workpiece 17, without the slide 11 undergoing any further radial advancing in the direction of the workpiece 17.

With the bending rollers 13 a radius 33 is formed in the circumferential edge region of the workpiece 17, the free edge of the aluminium cartridge 21 being shaped by the fact that it rests on the free end face of the plastic container. The shaping rollers 14 serve essentially to shape two encircling groove-like crimps 34 in a drawn neck region 35 of the workpiece 17.

The inhaler cartridge 36 is used in a nebuliser 37 which is used to nebulise a fluid 39, particularly a highly potent medicament, and is in the form of a portable inhaler that operates without propellant gas. When the fluid 2, preferably a liquid, is nebulised, an aerosol is formed which can be breathed in by a user (not shown).

The nebuliser 37 comprises the inhaler cartridge 36 holding the fluid 39, which can be inserted in the opened nebuliser 37 from below. In order to nebulise a predetermined adjustable amount of the fluid 39, the nebuliser 37 comprises a pressure generator 41 surrounding a piston, with a holder 42 for the inhaler cartridge 36, a drive spring 43 with a manually operated release button 44 for releasing the pressure, a conveying tube 40 with a non-return valve 45 inserted, a pressure chamber 46 and a nozzle 47, with which a mouthpiece 48 is associated.

As the drive spring 43 is axially tensioned by rotation of a lower housing part 49 with an inner part 50 releasably attached thereto, relative to an upper housing part 51 formed on the mouthpiece 48, the holder 42 is moved downwards with the inhaler cartridge 36 and the conveying tube 40 and fluid 39 is sucked out of the inhaler cartridge 36 through the non-return valve 45 into the pressure chamber 46 associated with the piston of the pressure generator 41. During the subsequent abrupt relaxation of the drive spring 43 by actuating the release button 44, the fluid 39 in the pressure chamber 46 is pressurised by the drive spring 43 moving the conveying tube 40 upwards and is expelled through the nozzle 47, whereupon nebulisation takes place. The nebulisation takes place for example in particles in the μm range, preferably in particles around 20 in size, which form a mist or jet of aerosol. A user is able to inhale the aerosol, while supply air can be sucked in through supply air openings 52 in the mouthpiece 48.

LIST OF REFERENCE NUMERALS

1. hollow shaft
2. rod
5. pressing member
6. conical region
7. carrier member
8. guide portion
9. lever
10. roller
11. slide
12. spindle
13. bending roller
14. shaping roller
15. depressor
16. arrow
17. workpiece
18. arrow
19. arrow
20. intermediate ring
21. aluminium cartridge
22. guide bolt
23. sliding bush
24. oblong hole
26. blind bore
27. swivel joint
28. pin
31. compression spring
32. cylindrical bolt
33. radius
34. crimp
35. neck region
36. inhaler cartridge
37. nebuliser
38. plastic container
39. fluid
40. conveying tube
41. pressure generator
42. holder
43. drive spring
44. release button
45. non-return valve
46. pressure chamber
47. nozzle
48. mouthpiece
49. lower housing part
50. inner part
51. upper housing part
52. supply air openings

We claim:

1. A shaping tool, comprising:

a rotatable base member having a plurality of profiled bending rollers that are mounted on a circular track and are rotatable about a rotation axis, each of the bending rollers being arranged on a respective radially movable slide that is movable from a first position that defines a maximum working aperture for the tool, radially inwardly to a second position that defines a minimum working aperture for the tool;

a plurality of lever arms, each lever arm including a first end, an opposing second end, and a fulcrum about which the lever arm rotates, the second end of each lever arm being coupled to a respective one of the slides such that:

(a) rotation of the lever arms in a first rotation direction causes: (i) the respective slides to move from the respective first positions radially inwardly toward the rotation axis of the rotatable base member to the respective second positions; and (ii) the respective profiled bending rollers to move toward one another and toward the rotation axis to achieve the minimum working aperture between the profiled bending rollers, and (b) rotation of the lever arms in an opposite, second rotation direction causes: (i) the respective slides to move from the respective second positions radially outwardly away from the rotation axis of the rotatable base member to the respective first positions; and (ii) the respective profiled bending rollers to move away from one another and away from the rotation axis to achieve the maximum working aperture between the profiled bending rollers, a pressing member engaging each of the first ends of the lever arms and operating to simultaneously rotate the lever arms about the respective fulcrums, in commanded ones of the first and second rotation directions, thereby causing the shaping tool to achieve commanded ones of the maximum and minimum working apertures, wherein at least an unformed portion of workpiece is disposed within the maximum working aperture, the base member is rotated, and the pressing member actuated such that the pressing member simultaneously rotates the lever arms about the respective fulcrums in the first rotation direction, and such that the profiled bending rollers move radially inwardly toward one another, toward the rotation axis, toward the minimum working aperture, and thereby rotationally engage the at least one unformed portion of the workpiece to produce a formed portion of the workpiece.

2. The shaping tool according to claim 1, further comprising a depressor disposed and movable in an axially aligned orientation with the rotational axis of the base member, and operating to hold the workpiece fixed during engagement of the profiled bending rollers.

3. The shaping tool according to claim 1, wherein:
the pressing member includes a conically shaped surface oriented axially with the rotational axis of the base member, and
each of the lever arms includes a roller at the first end thereof slidably engaging the conically shaped surface of the pressing member such that axial movement of the pressing member: (i) toward the base member causes the lever arms to simultaneously rotate in the first rotational direction, and (ii) away from the base member causes the lever arms to simultaneously rotate in the second rotational direction).

4. The shaping tool according to claim 3, further comprising a respective cylindrical bolt extending through a respective bore of each slide, and through a respective oblong hole of each lever arm.

5. The shaping tool according to claim 1, further comprising a carrier member to which each of the lever arms is pivotally coupled at the respective fulcrums.

6. The shaping tool according to claim 5, wherein each slide is slidably mounted on a respective pair of spaced-apart guide bolts in a respective guide portion of the base member, each guide portion being connected to the carrier member.

7. The shaping tool according to claim 1, wherein the pressing member is resiliently mounted in the axial direction.

8. The shaping tool according to claim 1, wherein at least one shaping roller for producing a crimp is rotatably mounted on a respective spindle of each slide, adjacent to the respective bending roller.

9. The shaping tool according to claim 1, wherein a cam roller cooperates with a cam control for the axial movement of the shaping tool.

10. The shaping tool according to claim 1, wherein three radially adjustable slides each having one of the lever arms are arranged in a star shape with one another.

11. The shaping tool according to claim 1, further comprising a retaining device operating to fix the workpiece coaxially with respect to a longitudinal axis along which the shaping tool travels, wherein the workpiece is an aluminum cartridge and a plastic container.

* * * * *

UNITED STATES PATENT AND TRADEMARK OFFICE
CERTIFICATE OF CORRECTION

| | | |
|---|---|---|
| PATENT NO. | : 8,495,901 B2 | Page 1 of 1 |
| APPLICATION NO. | : 12/748772 | |
| DATED | : July 30, 2013 | |
| INVENTOR(S) | : Hahn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this
Twenty-first Day of April, 2015

Michelle K. Lee
*Director of the United States Patent and Trademark Office*